United States Patent
Hu et al.

(10) Patent No.: US 12,068,074 B2
(45) Date of Patent: Aug. 20, 2024

(54) STEREOSCOPIC MARKER DEVICE AND THREE-DIMENSIONAL REAL-TIME POSITIONING METHOD OF ORTHOPEDIC SURGERY

(71) Applicant: METAL INDUSTRIES RESEARCH & DEVELOPMENT CENTRE, Kaohsiung (TW)

(72) Inventors: Po-Chi Hu, Kaohsiung (TW);
Yan-Ting Chen, Kaohsiung (TW);
Chin-Chung Lin, Kaohsiung (TW);
Wen-Hui Huang, Kaohsiung (TW);
Keng-Ta Lin, Kaohsiung (TW)

(73) Assignee: METAL INDUSTRIES RESEARCH & DEVELOPMENT CENTRE, Kaohsiung (TW)

( * ) Notice: Subject to any disclaimer, the term of this patent is extended or adjusted under 35 U.S.C. 154(b) by 877 days.

(21) Appl. No.: 17/064,069

(22) Filed: Oct. 6, 2020

(65) Prior Publication Data
US 2021/0174950 A1   Jun. 10, 2021

(30) Foreign Application Priority Data
Dec. 6, 2019   (TW) .................. 108144741

(51) Int. Cl.
*A61B 34/20*   (2016.01)
*A61B 17/70*   (2006.01)
(Continued)

(52) U.S. Cl.
CPC ............. *G16H 40/40* (2018.01); *A61B 17/70* (2013.01); *A61B 17/846* (2013.01); *A61B 34/20* (2016.02);
(Continued)

(58) Field of Classification Search
CPC ......... A61B 90/94; A61B 90/96; A61B 34/20; A61B 2034/2046; A61B 2034/2055; A61B 2034/2059
See application file for complete search history.

(56) References Cited

U.S. PATENT DOCUMENTS 5,394,875 A * 3/1995 Lewis .................... A61B 34/20
128/916
11,771,503 B1 * 10/2023 Henderson ............. A61B 34/20
606/102
(Continued)

FOREIGN PATENT DOCUMENTS

CN        106214256 A    12/2016

*Primary Examiner* — Eduardo C Robert
*Assistant Examiner* — Steven J Cotroneo
(74) *Attorney, Agent, or Firm* — WPAT, P.C

(57) ABSTRACT

A stereoscopic marker device includes: a polyhedral cube, including at least four flat surfaces, wherein the at least four flat surfaces are used as one primary marker and at least three secondary markers respectively, the primary marker includes a primary graphic code, the three secondary markers individually include a first secondary graphic code, a second secondary graphic code, and a third secondary graphic code, and the primary graphic code is used for providing spatial coordinate information, which is used for calculating six degrees of freedom (DOF) attitude data; and a spike-shaped body, combined with the polyhedral cube and configured to be fixed on a surgery site.

10 Claims, 4 Drawing Sheets

(51) Int. Cl.
*A61B 17/84* (2006.01)
*A61B 90/96* (2016.01)
*G06K 19/06* (2006.01)
*G16H 20/40* (2018.01)
*G16H 30/20* (2018.01)
*G16H 30/40* (2018.01)
*G16H 40/40* (2018.01)
*G16H 40/63* (2018.01)
*A61B 17/56* (2006.01)
*A61B 90/00* (2016.01)

(52) U.S. Cl.
CPC ........ A61B 90/96 (2016.02); G06K 19/06037 (2013.01); G16H 20/40 (2018.01); G16H 30/20 (2018.01); G16H 30/40 (2018.01); G16H 40/63 (2018.01); *A61B 2017/564* (2013.01); *A61B 2034/2057* (2016.02); *A61B 2090/3916* (2016.02); *A61B 2090/3937* (2016.02); *G06K 2019/06253* (2013.01)

(56) References Cited

U.S. PATENT DOCUMENTS

| 2019/0038362 | A1* | 2/2019 | Nash | A61B 34/25 |
| 2019/0336242 | A1* | 11/2019 | Daon | A61C 1/082 |
| 2021/0244481 | A1* | 8/2021 | Jaramaz | A61B 90/96 |
| 2021/0346117 | A1* | 11/2021 | Poltaretskyi | A61B 90/39 |
| 2021/0369353 | A1* | 12/2021 | Nikou | A61B 34/30 |
| 2022/0015835 | A1* | 1/2022 | Behera | A61B 90/90 |
| 2022/0151705 | A1* | 5/2022 | Nikou | A61B 90/361 |
| 2022/0265387 | A1* | 8/2022 | Daon | A61C 1/082 |
| 2023/0263541 | A1* | 8/2023 | Roussouly | A61B 34/20 606/80 |
| 2023/0285084 | A1* | 9/2023 | Mckinnon | G06N 5/046 703/11 |

* cited by examiner

STEREOSCOPIC MARKER DEVICE AND THREE-DIMENSIONAL REAL-TIME POSITIONING METHOD OF ORTHOPEDIC SURGERY

CROSS-REFERENCE TO RELATED APPLICATION

This application claims the benefit of Taiwan Patent Application No. 108144741, filed on Dec. 6, 2019, which is hereby incorporated by reference for all purposes as if fully set forth herein.

BACKGROUND

Technical Field

The present disclosure relates to a stereoscopic marker device and a three-dimensional real-time positioning method of orthopedic surgery, and in particular, to a three-dimensional real-time positioning method of orthopedic surgery by using a stereoscopic marker device.

Related Art

A surgical navigation system is an important development direction of precision and micro invasion of orthopedically surgical treatment, and an optical surgical navigation technology is most widely used. A pasted marker has smaller scratch and easier operation than a mechanical fixing device, is more precise than an anatomical marker, and is widely used. The optical surgical navigation system performs tracking and positioning by tracking points of the pasted marker on patients and surgical tools. The points of the pasted marker and a lesion position are determined by a three-dimensional medical image before surgery. The optical surgical navigation system tracks the points of the pasted marker on the patient by a positioning device in surgery, to obtain a posture of the patient in real time, and coverts the posture of the patient into an image coordinate system for display after three-dimensional medical image is registrated before the surgery.

The existing optical surgical navigation system has the following disadvantages: first, the points of the marker may fall during the surgical navigation process and needs to be re-registered; second, light reflected from the points of the marker may be obscured; in addition, some surgical sites are not convenient to paste the points of the marker.

China Patent Application Publication No. CN106214256A discloses a non-marker optical surgical navigation system and a navigation method thereof. The non-marker optical surgical navigation system includes a structured light three-dimensional scanning system, an optical positioning system, a calibration board, and a graphic workstation. The non-marker optical surgical navigation system continuously obtains surface information of a surgical area of a patient by using the structured light three-dimensional scanning system, thereby obtaining surface three-dimensional coordinates of the patient. A coordinate transformation relationship is obtained by using the surface three-dimensional coordinates of the patient in real time and the three-dimensional medical image registration of the patient before surgery. Meanwhile, a position of a surgical instrument is tracked in real time by using the near-infrared optical positioning system. Finally, the three-dimensional medical image of the surgical site of the patient and surgical tools are displayed on a display device. This patent document implements the optical surgical navigation of patients without marker, and does not require a doctor to manually register the marker. Therefore, an operation process and surgical time are reduced, a problem of falling of the marker is resolved, and meanwhile, use in an occasion in which some surgical sites are not convenient to paste the marker is facilitated.

However, lack of sufficient points of the marker in the patent document may result in lack of a direction in positioning, and therefore, precise positioning is impossible.

Therefore, a three-dimensional real-time positioning method of orthopedic surgery applied to a surgical navigation system needs to be provided, to resolve the foregoing problem.

SUMMARY

An objective of the present disclosure is to provide a three-dimensional real-time positioning method of orthopedic surgery by using a stereoscopic marker device.

To achieve the foregoing objective, the present disclosure discloses a stereoscopic marker device, comprising: a polyhedral cube, comprising at least four flat surfaces, wherein the at least four flat surfaces are used as one primary marker and at least three secondary markers respectively, the primary marker comprises a primary graphic code, the three secondary markers individually comprise a first secondary graphic code, a second secondary graphic code, and a third secondary graphic code, and the primary graphic code is used for providing spatial coordinate information, which is used for calculating six degrees of freedom (DOF) attitude data; and a spike-shaped body, combined with the polyhedral cube and configured to be fixed on a surgical site.

The present disclosure further discloses a three-dimensional real-time positioning method of orthopedic surgery, comprising the following steps: providing at least one stereoscopic marker device; fixing the at least one stereoscopic marker device on a surgical site; setting up an optical positioning system, wherein the optical positioning system comprises two six degrees of freedom (DOF) photographic devices, which are set as a primary photographic device and a secondary photographic device located at two sides of the surgical site respectively; calibrating the primary photographic device and the secondary photographic device; starting a six DOF calculation module; conforming that both of the primary photographic device and the secondary photographic device can recognize the polyhedral cube; determining whether the polyhedral cube of the stereoscopic marker device is obscured to cause the primary photographic device to fail in shooting; shooting the polyhedral cube of the stereoscopic marker device by using the primary photographic device when the polyhedral cube is not obscured; switching to shoot the polyhedral cube of the stereoscopic marker device by the secondary photographic device when the polyhedral cube is obscured; determining whether the primary marker of the polyhedral cube of the stereoscopic marker device is obscured to cause the primary photographic device or the secondary photographic device to fail in shooting; providing spatial coordinate information by using the primary graphic code of the primary marker when the primary marker is not obscured, to finish calculating six DOF attitude data; and calculating spatial coordinate information of the primary marker by using the first secondary graphic code to the third secondary graphic code of the three secondary markers when the primary marker is obscured, to finish calculating six DOF attitude data.

Beneficial effects of the present disclosure are as follows: First, the three-dimensional real-time positioning method of orthopedic surgery provided in the present disclosure can be a three-dimensional real-time positioning method of spine surgery, and the six DOF attitude data is calculated by the spike-shaped body (i.e., spinal spike) combined with the polyhedral cube (i.e., ceramic stereoscopic marker) to precisely position vertebral segment. After the six DOF photographic devices shoot the stereoscopic marker device a registration of the stereoscopic marker device is completed. A plurality of flat surfaces of different markers are set on the stereoscopic marker device on the spinal spike, and thus the six DOF attitude data (i.e., position data) of the stereoscopic marker device can be calculated when the six DOF photographic devices shoot one primary marker or three secondary markers of the polyhedral cube. Second, the concept of primary and secondary markers is introduced to the stereoscopic marker device of the present disclosure. When the primary marker is obscured, spatial coordinate information of the primary marker is calculated in real time by peripheral secondary markers, to ensure that precise positioning of surgical site is not affected when medical workers or other objects obscure the stereoscopic marker device. Third, the stereoscopic marker device of the present disclosure has a QR code feature, image recognition can be improved, and image capturing efficiency of the six DOF photographic devices is further improved. Fourth, the present disclosure develops the stereoscopic marker device having a QR code feature by using a special material, and three-dimensional spatial coordinate information can be defined by a single stereoscopic marker device. Fifth, the three-dimensional real-time positioning method of orthopedic surgery of the present disclosure can be applied to a surgery navigation system. Signals of the surgery navigation system cannot be interfered when the stereoscopic marker device of the present disclosure is obscured by medical workers or other objects, thereby increasing the movable position of medical workers or other objects in an operating room, and reducing restriction on the movement of the medical workers in the operating room.

DETAILED DESCRIPTION

To make the objectives, features, and characteristics of the present disclosure clearer and easier to understand, the following gives a detailed description of related embodiments of the present disclosure with reference to the accompanying drawings.

Figure 1:
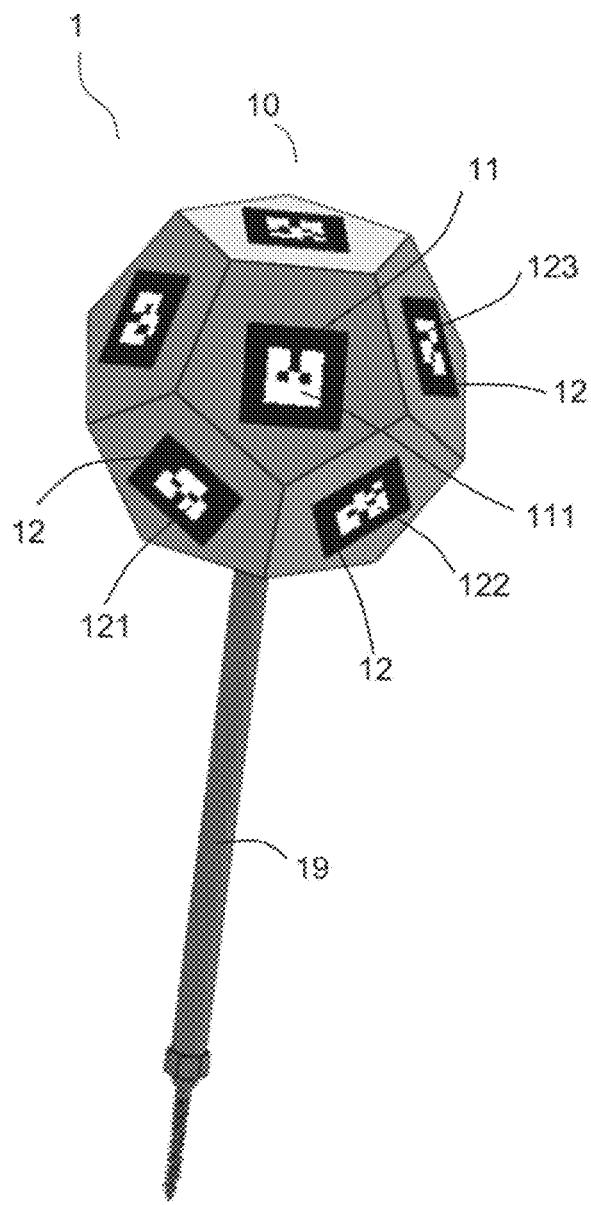
FIG. 1 is a schematic perspective view of a stereoscopic marker device according to an embodiment of the present disclosure.
Figure 2:
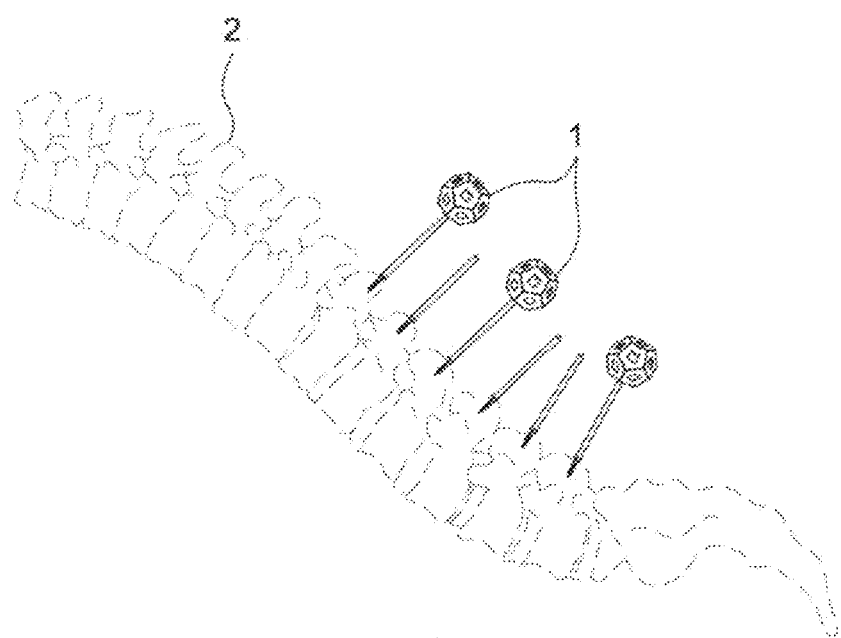
FIG. 2 is a schematic perspective view of a plurality of stereoscopic marker devices fixed on a surgical site according to an embodiment of the present disclosure.

FIG. 1 is a schematic perspective view of a stereoscopic marker device according to an embodiment of the present disclosure. FIG. 2 is a schematic perspective view of a plurality of stereoscopic marker devices fixed on a surgical site according to an embodiment of the present disclosure. The stereoscopic marker device 1 includes: a polyhedral cube 10 and a spike-shaped body 19. The spike-shaped body 19 is combined with the polyhedral cube 10 and configured to be fixed on a surgical site 2. When the surgical site 2 is a spine, the spike-shaped body 19 is a spinal spike.

The polyhedral cube 10 includes at least four flat surfaces, and the at least four flat surfaces are used as one primary marker 11 and at least three secondary markers 12 respectively. For example, the polyhedral cube 10 includes twelve flat surfaces, that is, the polyhedral cube 10 is a dodecahedral cube. The number of the at least three secondary markers 12 are eight. The primary marker 11 includes a primary graphic code 111, and the three secondary markers 12 individually include a first secondary graphic code 121, a second secondary graphic code 122, and a third secondary graphic code 123. In other words, the three secondary markers 12 can be first to third secondary markers, the first secondary marker includes the first secondary graphic code, 121, the second secondary marker includes the second secondary graphic code 122, and the third secondary marker includes the third secondary graphic code 123. The primary graphic code 111 is used for providing spatial coordinate information, which is used for calculating six degrees of freedom (DOF) attitude data. For example, an object has six DOF in space, that is, moving DOF along directions of three rectangular coordinate axes X, Y, and Z and rotating DOF around the three coordinate axes. The primary graphic code 111 and the first to the third secondary graphic codes 121, 122, and 123 are different quick response matrix graphic codes (QR codes).

A material of the polyhedral cube 10 of the stereoscopic marker device 1 can be a plastic medical material such as poly-ether-ether-ketone (PEEK). Alternatively, a material of the polyhedral cube 110 can be a ceramic material such as aluminum oxide. For example, a powder die-casting sintering process of the polyhedral cube 110 of the stereoscopic marker device 1 is as follows: First, a ceramic block material in accordance with recognition of an infrared ray (IR) light source is developed in a specific proportion formula of aluminum oxide material and adhesive. Second, the manufactured ceramic block material is ground by a diamond grinding wheel to manufacture the stereoscopic marker device required for a six DOF tracking technology. Finally, a quick response matrix graphic code (QR) code feature is processed on a surface of the polyhedral cube made of aluminum oxide by using a laser process.

Figure 3:
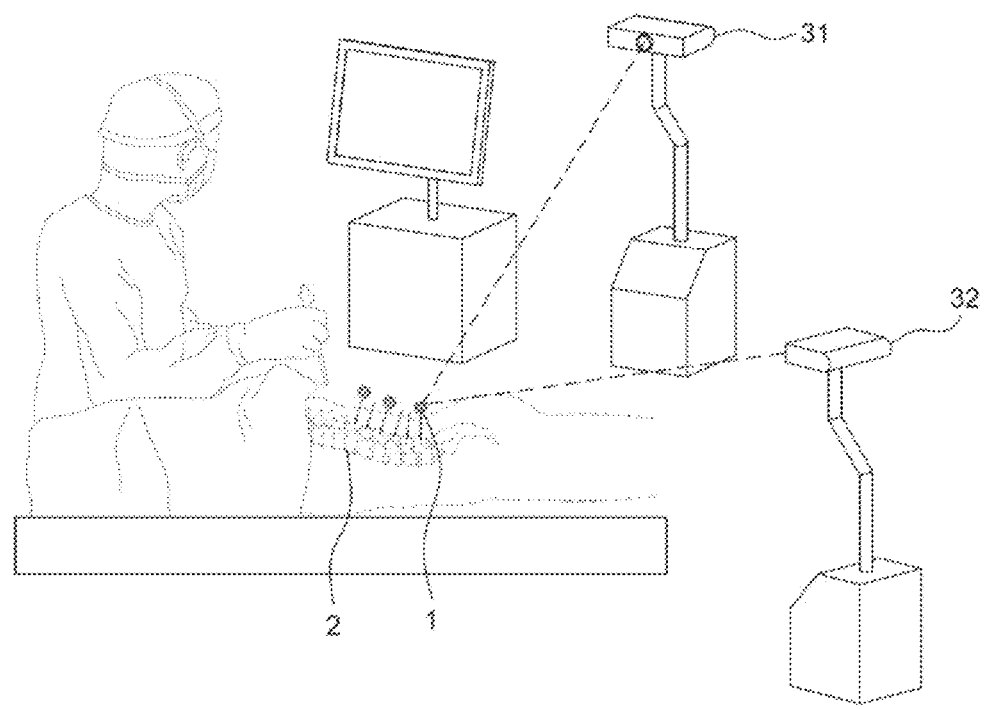
FIG. 3 is a schematic perspective view of orthopedic surgery by using a plurality of stereoscopic marker devices fixed on a surgical site according to an embodiment of the present disclosure.
Figure 4:
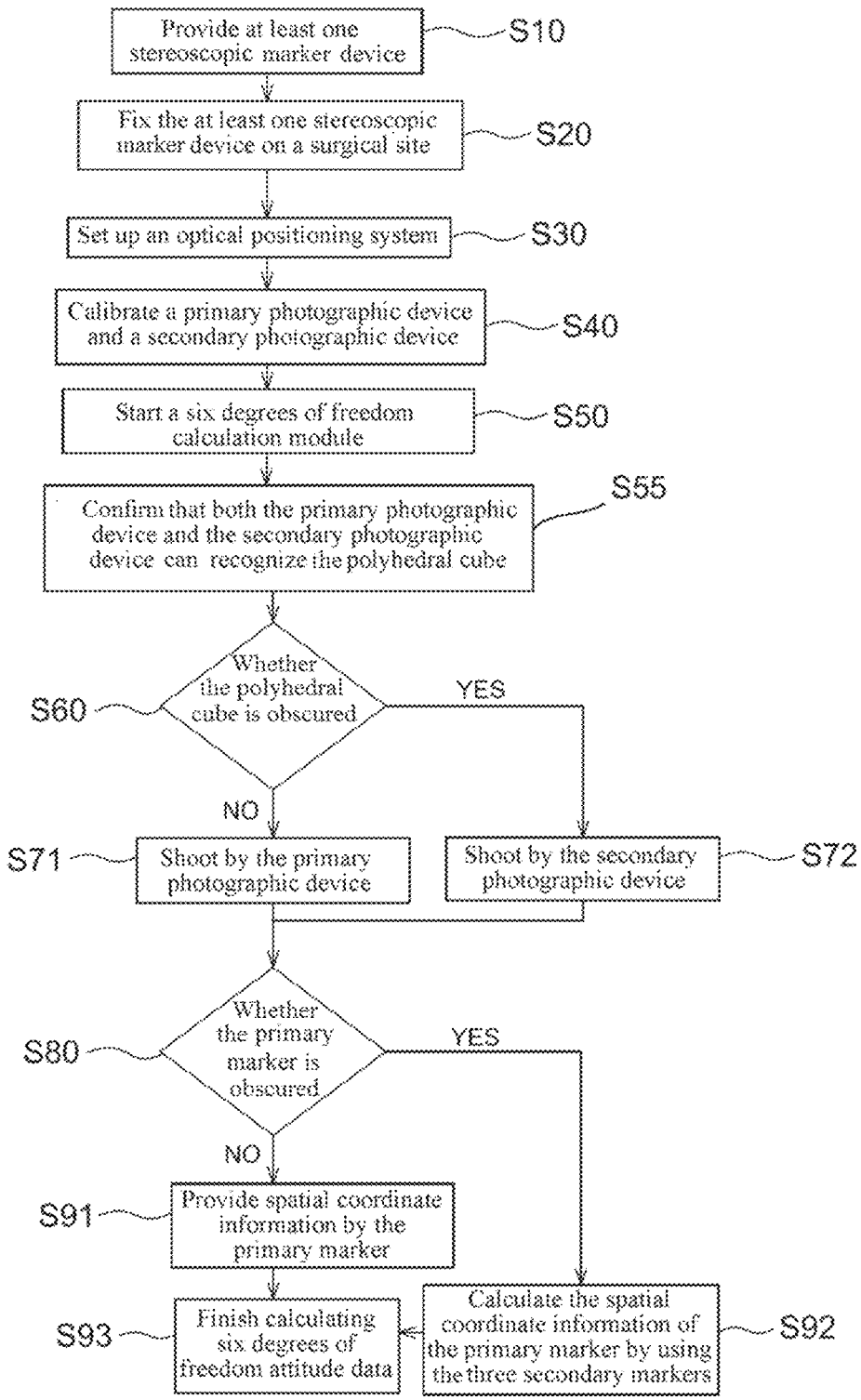
FIG. 4 is a flow chart of a three-dimensional real-time positioning method of orthopedic surgery according to an embodiment of the present disclosure.

FIG. 3 is a schematic perspective view of orthopedic surgery according to an embodiment of the present disclosure. FIG. 4 is a flow chart of a three-dimensional real-time positioning method of orthopedic surgery according to an embodiment of the present disclosure. The three-dimensional real-time positioning method of orthopedic surgery includes the following steps.

Step S10. Provide the foregoing at least one stereoscopic marker device 1 of the present disclosure. Referring to FIG. 1, the stereoscopic marker device 1 includes: a polyhedral cube 10 and a spike-shaped body 19. The polyhedral cube 10 includes at least four flat surfaces, and the at least four flat surfaces are used as one primary marker 11 and at least three secondary markers 12 respectively. The primary marker 11 includes a primary graphic code 111, and the three secondary markers 12 individually include a first secondary graphic code 121, a second secondary graphic code 122, and a third secondary graphic code 123. The primary graphic code 111 and the first to the third secondary graphic codes 121, 122, and 123 are different QR codes.

Step S20. Fix the at least one stereoscopic marker device 1 on a surgical site 2. When the surgical site 2 is a spine, a plurality of stereoscopic marker devices 1 are fixed on the surgical site 2 by the spike-shaped body 19 (that is, a spinal spike). Step S30. Set up an optical positioning system. The optical positioning system includes two six DOF photographic devices, which are set as a primary photographic device 31 and a secondary photographic device 32 located at two sides of the surgical site 2 respectively. Step S40. Calibrate the primary photographic device 31 and the secondary photographic device 32. Step S50. Start a six DOF calculation module. The six DOF calculation module can be a processor having a calculation function.

Step S55. Confirm that both of the primary photographic device 31 and the secondary photographic device 32 can recognize the polyhedral cube. After software of the six DOF calculation module is started for the first time, subsequent procedures (steps S60 to S71/S72) can be continued only after it is determined that both of the primary photographic device 31 and the secondary photographic device 32 can recognize the polyhedral cube 10 of the stereoscopic marker device 1. If one of the primary photographic device 31 and the secondary photographic device 32 cannot recognize the polyhedral cube 10, positions of the primary photographic device 31 and the secondary photographic device 32 need to be adjusted until the polyhedral cube is visible to both of the primary and secondary photographic devices 31, 32. Step S60. Determine whether the polyhedral cube 10 of the stereoscopic marker device 1 is obscured to cause the primary photographic device 31 to fail in shooting. Step S71. Shoot the polyhedral cube 10 of the stereoscopic marker device 1 by the primary photographic device 31 when the polyhedral cube 10 of the stereoscopic marker device 1 is not obscured. Step S72. Switch to shoot the polyhedral cube 10 of the stereoscopic marker device 1 by the secondary photographic device 32 when the polyhedral cube 10 of the stereoscopic marker device 1 is obscured. When the primary photographic device 31 or the secondary photographic device 32 shoots the polyhedral cube 10 of the stereoscopic marker device 1, a registration of the stereoscopic marker device 1 is completed.

Step S80. Determine whether the primary marker 11 of the polyhedral cube 10 of the stereoscopic marker device 1 is obscured to cause the primary photographic device 31 or the secondary photographic device 32 to fail in shooting. Step S91. Provide spatial coordinate information by using the primary graphic code of the primary marker 11 when the primary marker 11 is not obscured, to enter step S93: Finish calculating six DOF attitude data. Step S92. Calculate spatial coordinate information of the primary marker 11 by using the first to the third secondary graphic codes 121, 122, and 123 of the three secondary markers 12 when the primary marker 11 is obscured, to enter step S93: Finish calculating six DOF attitude data.

In this embodiment, a conversion is performed between an image coordinate system and a world coordinate system (WCS) by using a transposed matrix, to calculate the six DOF attitude spatial data (for example, an object has six DOF in space, that is, moving DOF along directions of three rectangular coordinate axes X, Y, and Z and rotating DOF around the three coordinate axes). For example, first, a WCS, a photographic device coordinate system, and an image coordinate system are defined, wherein the WCS is a common coordinate system. Then, image data shot by the photographic device is converted from the image coordinate system to the photographic device coordinate system, and converted from the photographic device coordinate system to the WCS. Through this conversion step, all coordinate values and vectors can be calculated with each other. In a traditional practice, after an origin of the WCS is preset in space, a position of the photographic device in the WCS and inner parameters of the photographic device are calibrated, to convert a coordinate value of a two-dimensional image shot by the photographic device into a world coordinate value of three-dimensional space, so that all coordinate systems can be converted with each other. A conversion relationship between the image coordinate system and the WCS is the transposed matrix, and moving DOF along directions of three rectangular coordinate axes X, Y, and Z and rotating DOF around the three coordinate axes of the object shot by the photographic device can be calculated by using the transposed matrix.

Beneficial effects of the present disclosure are as follows: First, the three-dimensional real-time positioning method of orthopedic surgery provided in the present disclosure can be a three-dimensional real-time positioning method of spine surgery, and the six DOF attitude data is calculated by the spike-shaped body (i.e., spinal spike) combined with the polyhedral cube (i.e., ceramic stereoscopic marker) to precisely position vertebral segment. After the six DOF photographic devices shoot the stereoscopic marker device a registration of the stereoscopic marker device is completed. A plurality of flat surfaces of different markers are set on the stereoscopic marker device on the spinal spike, and thus the six DOF attitude data (i.e., position data) of the stereoscopic marker device can be calculated when the six DOF photographic devices shoot one primary marker or three secondary markers of the polyhedral cube.

Second, the concept of primary and secondary markers is introduced to the stereoscopic marker device of the present disclosure. When the primary marker is obscured, spatial coordinate information of the primary marker is calculated in real time by peripheral secondary markers, to ensure that precise positioning of surgical site is not affected when medical workers or other objects obscure the stereoscopic marker device.

Third, the stereoscopic marker device of the present disclosure has a QR code feature, image recognition can be improved, and image capturing efficiency of the six DOF photographic devices is further improved.

Fourth, the present disclosure develops the stereoscopic marker device having a QR code feature by using a special material, and three-dimensional spatial coordinate information can be defined by a single stereoscopic marker device.

Fifth, the three-dimensional real-time positioning method of orthopedic surgery of the present disclosure can be applied to a surgery navigation system. Signals of the surgery navigation system cannot be interfered when the stereoscopic marker device of the present disclosure is obscured by medical workers or other objects, thereby increasing the movable position of medical workers or other objects in an operating room, and reducing restriction on the movement of the medical workers in the operating room.

In conclusion, it is only a description of preferred implementations or embodiments of the technical means adopted by the present disclosure to resolve the problem, and is not intended to limit the scope of patent implementation of the present disclosure. That is, all variations and modifications that are consistent with the meaning of the scope of the claims of the present disclosure, or made according to the scope of the claims of the present disclosure, are covered by the scope of the claims of the present disclosure.

What is claimed is:

1. A stereoscopic marker device, comprising:
   a polyhedral cube, being a dodecahedral cube and comprising twelve flat surfaces, wherein the twelve flat surfaces are used as one primary marker and eight secondary markers respectively, the primary marker comprises a primary graphic code, at least three of the eight secondary markers individually comprise a first secondary graphic code, a second secondary graphic code, and a third secondary graphic code, and the primary graphic code is used for providing spatial coordinate information, which is used for calculating six degrees of freedom (DOF) attitude data; and
   a spike-shaped body, combined with the polyhedral cube and configured to be fixed on a surgical site;
   wherein when the primary graphic code of the primary marker of the polyhedral cube is obscured, one of a primary photographic device and a secondary photographic device must recognize the first to the third secondary graphic codes of the at least three secondary markers of the polyhedral cube.

2. The stereoscopic marker device according to claim 1, wherein the primary graphic code and the first secondary graphic code to the third secondary graphic code are different quick response matrix graphic codes.

3. The stereoscopic marker device according to claim 2, wherein a material of the polyhedral cube is a ceramic material or a plastic medical material.

4. The stereoscopic marker device according to claim 1, wherein when the surgical site is a spine, the spike-shaped body is a spinal spike.

5. A three-dimensional real-time positioning method of orthopedic surgery, comprising the following steps:
   providing at least one stereoscopic marker device according to claim 1;
   fixing the at least one stereoscopic marker device on a surgical site;
   setting up an optical positioning system, wherein the optical positioning system comprises two six degrees of freedom (DOF) photographic devices, which are set as a primary photographic device and a secondary photographic device located at two sides of the surgical site respectively;
   calibrating the primary photographic device and the secondary photographic device;
   starting a six DOF calculation module;
   conforming that both of the primary photographic device and the secondary photographic device can recognize the polyhedral cube;
   determining whether the polyhedral cube of the stereoscopic marker device is obscured to cause the primary photographic device to fail in shooting;
   shooting the polyhedral cube of the stereoscopic marker device by using the primary photographic device when the polyhedral cube is not obscured;
   switching to shoot the polyhedral cube of the stereoscopic marker device by the secondary photographic device when the polyhedral cube is obscured;
   determining whether the primary marker of the polyhedral cube of the stereoscopic marker device is obscured to cause the primary photographic device or the secondary photographic device to fail in shooting;
   providing spatial coordinate information by using the primary graphic code of the primary marker when the primary marker is not obscured, to finish calculating six DOF attitude data; and
   calculating spatial coordinate information of the primary marker by using the first secondary graphic code to the third secondary graphic code of the three secondary markers when the primary marker is obscured, to finish calculating six DOF attitude data.

6. The three-dimensional real-time positioning method of orthopedic surgery according to claim 5, wherein a conversion is performed between an image coordinate system and a world coordinate system (WCS) by using a transposed matrix, to calculate the six DOF attitude data.

7. The three-dimensional real-time positioning method of orthopedic surgery according to claim 5, wherein the primary graphic code and the first secondary graphic code to the third secondary graphic code are different quick response matrix graphic codes.

8. The three-dimensional real-time positioning method of orthopedic surgery according to claim 7, wherein a material of the polyhedral cube is a ceramic material or a plastic medical material.

9. The three-dimensional real-time positioning method of orthopedic surgery according to claim 8, wherein the ceramic material is aluminum oxide, and the polyhedral cube is manufactured by a powder die-casting and sintering process, a grinding process, and a laser process.

10. The three-dimensional real-time positioning method of orthopedic surgery according to claim 5, wherein when the surgical site is a spine, the spike-shaped body is a spinal spike.

\* \* \* \* \*